United States Patent [19]
Nitelea et al.

[11] 4,150,023
[45] Apr. 17, 1979

[54] HYDROSOLUBLE RIFAMYCINS AND PROCESS FOR THEIR PREPARATION

[75] Inventors: Ion Nitelea, Bucharest; Alexandru Sauciuc, Iasi; Eugeniu Paunescu, Bucharest; Margareta Albu; Constantin Diaconescu, both of Iasi, all of Romania

[73] Assignee: Intreprinderea de Antibiotice Iasi, Iasi, Romania

[21] Appl. No.: 812,428

[22] Filed: Jul. 1, 1977

[51] Int. Cl.$^2$ ............................................. C07D 498/08
[52] U.S. Cl. ............................... 260/239.3 P; 424/244
[58] Field of Search ................................... 260/239.3 P

[56] References Cited

U.S. PATENT DOCUMENTS

| 3,342,810 | 9/1967 | Maggi et al. | 260/239.3 P |
| 3,862,934 | 1/1975 | Cricchio et al. | 260/239.3 P |
| 3,933,800 | 1/1976 | Cricchio et al. | 260/239.3 P |
| 4,005,076 | 1/1977 | Cricchio et al. | 260/239.3 P |

OTHER PUBLICATIONS

Burger, "Medicinal Chemistry" 2nd Ed. (1960), (Interscience) pp. 46-71.

Primary Examiner—Henry R. Jiles
Assistant Examiner—Robert T. Bond
Attorney, Agent, or Firm—Karl F. Ross

[57] ABSTRACT

This application relates to hydrosoluble rifamycins consisting of a molecular associations between a rifamycin derivative and an alkaline salt of an organic acid in a molar ratio 1 rifamycin to 0.5 to 5 alkali metal salt. These hydrosoluble rifamycins are obtained by solubilization of the respective rifamycin derivatives with the selected solubilizing agent, in a suitable organic solvent and they are isolated through dilution with a hydrocarbon, after a vacuum concentration by filtration and drying, or through evaporation. These products realize a prolonged gutliver recycling and a lower toxicity, against the liver cell.

11 Claims, No Drawings

HYDROSOLUBLE RIFAMYCINS AND PROCESS FOR THEIR PREPARATION

The present application refers to hydrosoluble rifamycins and to a process for their preparation.

Research during the last years showed the ability of certain derivatives of rifamycins to achieve a wide variety of biological effects: antibacterial and especially antituberculous, antiviral, immunesupressive, antileukemic, etc. which pointed out the possibility to utilize some of such derivatives in human therapy.

In order to obtain rifamycin derivatives which exhibit a biological activity, a number of procedures for its preparation have been used (Romanian application: No. 62778 and 62437). These procedures have a common disadvantage: in that they head to some slightly soluble substances, or insoluble altogether in aqueous media, raising difficulties in determining of biological activities and represent a limiting factor in absorption through the gut after oral administration.

Today, with some exceptions, the biological activities tests of rifamycin derivatives are performed after a previous dissolution in the presence of dimethylsulfoxide or detergents, but the detergents and dimethylsulfoxide have toxic effects which bring, during the tests, additional effects leading to non conclusive results.

Preparation of insoluble rifamycin derivatives in saline solutions involve a limitation of testing their activities, which nowadays is required in enzymatic systems as purified nucleic polymerases. Such methodology is not sufficient, because in human use the rifamycin derivatives exhibit their activity at the cellular level, where they will interact with different membranous structures, through which they must penetrate without any alteration of the normal cellular functions, and without lessening their inhibitory potential against the pathogenic modified cells.

The test of biological effects of rifamycin derivatives dissolved in the presence of dimethylsulfoxide or of detergents, do not allow a differentiation among their activity on normal cells, and that on pathologically altered cells, while the solubilizing additives have direct toxic effects on both types of cells, the presence of only dimethylsulfoxide or only of detergents, affects the main metabolic pathways (protein DNA and RNA) in both normal and pathological cells.

In such conditions, the same derivative may be considered stronger if it is tested after dissolutions in dimethylsulfoxide, and weaker when it is tested without dimethylsulfoxide, and shows clearly the possibility of some erroneous conclusions based on experimental data obtained by using some rifamycin derivatives with very slight solubility in saline solutions.

To yield certain rifamycin derivatives with a good solubility in saline solutions is very important, not only to ensure the correct conditions needed to test different biological effects, but also for augmentation of their therapeutic activity. As is known, because of their selective solubility in bile, the rifampicin derivatives perform an enterohepatic circuit, which ensures a prolonged persistance of them in the body, but at the same time an unpleasant and dangerous long span charge of liver is generated together with a biliar solubility threshold rising of bilirubin and related metabolites. Such hepato-biliary alterations affect a large number of ill subjects treated with rifampicin and is the cause of some over 10% unsuccessful therapeutic treatments which could be completely avoided by introduction of some solubilized forms of rifamycin in therapy.

The hydrosoluble rifamycins, according to this application, exclude the disadvantages above mentioned, through a higher solubility in order to obtain a good resorption in water, they have a chemical structure according to the formula (I).

$$R . A_n \qquad (I)$$

where R represents the derivative molecule of rifamycin selected among hydrazones, acylhydrazones and oximes of 3-formylrifamycin SV, A represents the salt molecule of an organic acid which may be an aliphatic one with a chain of 1 to 16 carbons (normal or branched), or an aromatic acide unsubstituted, or ring substituted, or an acid, with a steroid structure, and n represents the number of salt molecules and may be ranged between 0.5 and 5. They are amorphous substances or microcrystalline, orange colored to dark red-brown, very soluble in halogenate hydrocarbons, soluble in water and lower aliphatic alchools, slightly soluble in aliphatic hydrocarbons; the procedure of their preparation consists of the contact of the rifamycin derivative R with the salt solution A and then they are allowed to react in a solvent selected among aliphatic alchools with 1 to 8 carbons or aliphatic halogenated hydrocarbons with 1 to 3 carbons, or with a mixture of them, using the solubilized salt in a ratio of 0.5 to 5 mol to one mol of rifamycin derivative. The final product is then isolated by simple dilution of the reaction mass, or after concentration under vacuum, with an aliphatic or aromatic hydrocarbon in a ratio of 3 to 20 volumes, followed by filtration and drying of a solid product or by separation through decantation of oily phase (layer) which is dryed and ground, or it is isolated through solvent evaporation from the reaction mass and the product is ground.

In the following lines we present 15 examples.

EXAMPLE 1

Rifampicin - sodium ethylhexanoate.

In 4 ml of chloroform are dissolved 823 mg (1 mmol rifampicin). To add 1 ml isopropanol solution 2 M of sodium hexanoate (2 mmol). After 30 min. the resulted solution is brought under stirring in 30 ml petroleum-ether. After about 1 hour the solution is filtered, washed with petroleum-ether and dried. Results 730 ml of product with 79% rifampicin: yield=70%.

Instead of petroleum-ether an aliphatic or aromatic hydrocarbonate may be used in order to dilute the reaction mass. In a pH 7 phosphate buffer in 15 minutes over 100 mg product per ml can be dissolved.

By a similar procedure, but with 0.5 ml ethylhexanoate solution (1 mmol) one obtains 600 mg product with 84% rifampicin; yield is 61%, solubility 4.5 mg product per ml.

Similarly, with 1.5 ml sodium ethylhexanoate (3 mmol), 735 product is obtained having 79% rifampicin.

EXAMPLE 2

Rifampicin - sodium taurocholate

The procedure is similar with that described in example 1, using a solution of 538 mg (1 mmol) sodium taurocholate in 10 ml methanol. After dilution in 60 ml petroleum-ether, the resulting oleous layer, which is separated by decantation and dried under vacuum, leads to 1.12 g product; yield is 82%. The solubility is 41 mg per ml.

EXAMPLE 3

Rifampicin - sodium desoxycholate.

In 10 ml methanol are dissolved 930 ml (2 mmol) sodium desoxycholate and 823 mg (1 mmol) rifampicin which are concentrated under vacuum to 1/3 volume; then over 50 ml petroleum-ether are added to separate the oleous layer and all is allowed to dry. Results are 1.4 g product with 46% rifampicin content. The yield is 78%. The product's solubility is over 100 mg per ml.

By a similar procedure, with 415 ml (1 mmol) sodium desoxycholate, 920 mg of product are obtained, with 72% rifampicin content. The yield is 80%. The product is soluble in a ratio of 30 mg per ml.

Instead of methanol as solvent another alkanol with no more than 8 carbons in the molecule may be used.

EXAMPLE 4

Rifampicin - sodium benzoate.

In 20 ml methanol, 288 mg (2 mmol) sodium benzoate and 823 mg (1 mmol) rifampicin are dissolved. The resulted solution is concentrated under vacuum up to one third volume, then precipitated with 50 ml petroleum-ether. Then it is filtered and dried. Results 900 mg product; yield is 80%. The product's solubility in a phosphate buffer is 4.5 mg per ml.

EXAMPLE 5

Rifampicin - sodium acetate.

The procedure is similar to that described in example 4, using 164 mg (2 mmol) sodium acetate dissolved in 4 ml methanol. Without concentration step, to precipitate the product in 70 ml petroleum-ether. The oleous layer is solidified in two hours, then dried. One obtains 850 mg product, the yield is 85%. The solubility is 13.5 mg per ml.

EXAMPLE 6

Rifampicin - sodium caproate.

The procedure is similar to that described in example 4 using 276 mg (2 mmol) sodium caproate dissolved in 10 ml methanol and to precipitate the product with 100 ml petroleum-ether without a previous concentration. The oleous sediment hardens in approx. 2 hours. Drying under vacuum, 620 mg of product are obtained. The yield is 56%. The product's solubility is over 100 mg per ml.

As it can be seen from the examples, the rifamycin derivative is dissolved just at the moment when it is brought into contact with the salt A or it is previously dissolved and then is subjected to a treatment with salt A.

EXAMPLES 7-15. - Other rifamycins - soluble forms.

When the work is carried out as in above mentioned examples, using 2 mol of sodium ethylhexanoate versus 1 mol of rifamycin derivative, the soluble forms of other derivatives, presented in Table 1, are obtained using the specific volumes of solvent, and resulting in the products characterized by the main proprieties tabulated.

TABLE 1

| Example Rifamycin Derivative No. | Vol. of Chloroform Needed To Dissolve 1 mmol (ml) | Vol. of Petroleum Ether For Prepp. (ml) | Resulted Product (mg) | Yield % | Solubility (mg/ml) | | Decomposition Temperature Or Melting Point With Decomposition (° C.) |
|---|---|---|---|---|---|---|---|
| | | | | | as such | soluble form | |
| 7. 3-formylrifamycin SV oxime | 5 | 15 | 640 | 50 | 5.5 | over 100 | 176-187 |
| 8. 3-formylrifamycin SV oxime (K salt) | 5 | 15 | 650 | 59 | 5.5 | 25 | 190-195 |
| 9. 3-(ethyloximinomethyl)rifamycin SV | 5 | 60 | 705 | 64 | 0.12 | over 100 | 190-195 |
| 10. 3-(2-bromethyloximinomethyl)-rifamycin SV | 5 | 60 | 950 | 80 | 2.95 | over 100 | 185-190 |
| 11. 3-[3'-(p-tolyl)-pyridazinyl-6'-hydrazonomethyl]-rifamycin SV | 7 | 40 | 910 | 81 | 0.27 | 0.54 | 200-204 |
| 12. 3-[3'-(3'',4''-dimethylphenyl)-pyridazinyl-6'-hydrazonomethyl]-rifamycin SV | 7 | 40 | 920 | 80 | under 0.1 | 0.54 | 184-187 |
| 13. 3-(isonicotinoylhydrazonomethyl)-rifamycin SV | 12 | 60 | 1020 | 87 | 0.92 | 168 | 198-202 |
| 14. 3-(phenylacetylhydrazonomethyl)-rifamycin SV | 7 | 50 | 910 | 84 | 4.8 | 71 | 195-200 (melt) |
| 15. 3-phenoxyacetylhydrazonomethyl)-rifamysin SV | 8 | 50 | 960 | 87 | 2.75 | 128 | 207-210 (melt) |

Similar to working procedure from examples, all products represented by formula I are prepared.

As it can be seen from examples presented in this application, the application is based on the fact that a series of alkaline salts of organic acids combined with rifamycin derivatives enhance in substantial amounts the solubility in water. It was established also that the solubility of the new products is in a relationship with the molar ratio of solubilizing agent versus the rifamycin derivative, and also with the particular organic acid used.

These statements are presented in the Table 2.

Table 2

The solubility of different forms of soluble rifamycin in phosphate buffer at pH = 7

| No. Solubilizing agent | Molar ratio of solubilizing agent versus rifamycin | Solubility (15 min. saturation) (mg/ml) |
|---|---|---|
| 0. Blank | — | 2.5 |
| 1. Sodium acetate | 2 | 13.5 |
| 2. Sodium benzoate | 2 | 4.5 |
| 3. Sodium caproate | 2 | over 100 |
| 4. Sodium taurocholate | 1 | 41 |
| 5. Sodium desoxycholate | 1 | 30 |
| 6. Sodium desoxycholate | 2 | over 100 |
| 7. Sodium 2-ethylhexanoate | 1 | 4.5 |
| 8. Sodium 2-ethylhexanoate | 2 | over 100 |

We claim:

1. A hydrosoluble rifamycin of the following formula:

$R-A_n$ wherein R is a hydrazone, acylhydrazone, or oxime of 3-formylrifamycin SV, A is an anion of an alkali metal salt of a $C_1$ to $C_{16}$ normal or branched chain aliphatic acid, an aromatic acid, a substituted aromatic acid or a steroid acid and n is from 0.5 to 5, R being selected from the group which consists of:
  rifampicin
  3-formylrifamycin SV oxime
  3-(ethyloximinomethyl)-rifamycin SV
  3-(2-bromoethyloximinomethyl)-rifamycin SV
  3-[3'-(p-tolyl)-pyridazinyl-6'-hydrazonomethyl]-rifamycin SV
  3-[3'-(3",4"-dimethylphenyl)-7-pyridazinyl-6'-hydrazonomethyl]-rifamycin SV
  3-(isonicotinoyl-hydrazonomethyl)-rifamycin SV
  3-(phenylacetyl-hydrazonomethyl)-rifamycin SV; and
  3-(phenoxyacetyl-hydrazonomethyl-rifamycin SV.

2. The rifamycin defined in claim 1 wherein R is rifampicin.

3. The rifamycin defined in claim 1 wherein R is 3-formylrifamycin SV oxime.

4. The rifamycin defined in claim 1 wherein R is 3-(ethyloximinomethyl)-rifamycin SV.

5. The rifamycin defined in claim 1 wherein R is 3-(2-bromoethyloximinomethyl)-rifamycin SV.

6. The rifamycin defined in claim 1 wherein R is 3-[3'-(p-tolyl)-pyridazinyl-6'-hydrazonomethyl]-rifamycin SV.

7. The rifamycin defined in claim 1 wherein R is 3-[3'-(3",4"-dimethylphenyl)-7-pyridazinyl-6'-hydrazonomethyl]-rifamycin SV.

8. The rifamycin defined in claim 1 wherein R is 3-(isonicotinoyl-hydrazonomethyl)-rifamycin SV.

9. The rifamycin defined in claim 1 wherein R is 3-(phenyl-acetyl-hydrazonomethyl)-rifamycin SV.

10. The rifamycin defined in claim 1 wherein R is 3-(phenoxyacetyl-hydrazonomethyl)-rifamycin SV.

11. A process for preparing a hydrosoluble rifamycin of the following formula:

$R-A_n$ wherein R is a hydrazone, acylhydrazone or oxime of 3-formylrifamycin SV, A is an anion of an alkali metal salt of a $C_1$ to $C_{16}$ normal or branched chain aliphatic acid, an aromatic acid, a substituted aromatic acid or a steroid acid and n is from 0.5 to 5, which comprises the step of:
  reacting a hydrazone, acylhydrazone, or oxime of 3-formyl-rifamycin SV with an alkali metal salt of a $C_1$ to $C_{16}$ normal or branced chain aliphatic acid, aromatic acid, substituted aromatic acid or a steroid acid in a solvent selected from the group consisting of $C_1$ to $C_8$ aliphatic alcohols, $C_1$ to $C_3$ halocarbons and mixtures of both wherein the molar ratio of the alkali metal salt to the rifamycin is from 0.5 to 5 alkali metal salt to 1 rifamycin, R being selected from the group which consists of:
rifampicin
3-formylrifamycin SV oxime
3-(ethyloximinomethyl)-rifamycin SV
3-(2-bromoethyloximinomethyl)-rifamycin SV
3-[3'-(p-tolyl)-pyridazinyl-6'-hydrazonomethyl]-rifamycin SV
3-[3'-(3",4"-dimethylphenyl)-7-pyridazinyl-6'-hydrazonomethyl]-rifamycin SV
3-(isonicotinoyl-hydrazonomethyl)-rifamycin SV
3-(phenylacetyl-hydrazonomethyl)-rifamycin SV; and
3-(phenoxyacetyl-hydrazonomethyl-rifamycin SV.

* * * * *